United States Patent [19]

Binnig et al.

[11] 3,962,449
[45] June 8, 1976

[54] CARDIOACTIVE BISPIDONES AND BISPIDINES

[75] Inventors: Fritz Binnig, Fussgoennheim; Manfred Raschack, Weisenheim am Sand; Hans-Joerg Treiber, Bruehl, all of Germany

[73] Assignee: Knoll A.G. Chemische Fabriken, Ludwigshafen (Rhine), Germany

[22] Filed: June 10, 1975

[21] Appl. No.: 585,606

[30] Foreign Application Priority Data
June 14, 1974 Germany............................ 2428792

[52] U.S. Cl............................ 424/267; 260/293.55
[51] Int. Cl.²......................................... C07D 227/04
[58] Field of Search................ 260/293.55; 424/267

[56] References Cited
UNITED STATES PATENTS
3,167,561  1/1965  Sarett et al. ........................ 260/293

OTHER PUBLICATIONS
Douglas et al., J. Org. Chem. 33 (1), 355–359 (1968).

*Primary Examiner*—G. Thomas Todd
*Attorney, Agent, or Firm*—Curtis, Morris & Safford

[57] ABSTRACT

Cardioactive bispidones and bispidines of the formula

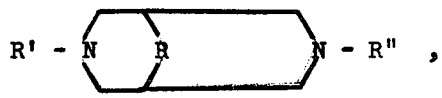

wherein R is =C=O or —CH$_2$— and R' and R'' are alkyl mono- or di-substituted by phenyl, made by a Mannich reaction from formaldehyde, piperidones of the formula

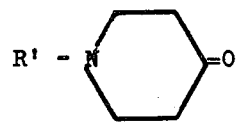

and amines of the formula R''—NH$_2$.

15 Claims, No Drawings

CARDIOACTIVE BISPIDONES AND BISPIDINES

The present invention relates to compounds of the formula

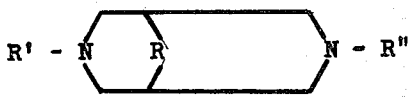

wherein R represents a C=O or CH$_2$ group, R' represents lower alkyl, suitably containing 1 to 4 carbon atoms and optionally substituted by a phenyl group, and R'' represents lower alkyl, suitably containing from 1 to 6 carbon atoms and optionally substituted by one or two phenyl groups, with the proviso that R' and R'' together contain at least six carbon atoms, to pharmacologically acceptable salts of such compounds, and to pharmaceutical compositions containing at least one of these compounds.

The compounds are prepared by subjecting a compound of the formula

wherein R' is as defined above, to a Mannich reaction with formaldehyde and an amine of the formula R'λ'—NH$_2$, wherein R'' is as defined above, to form such a bispidone compound in which R represents a C=O group, the corresponding bispidine compounds in which R represents a CH$_2$ group being prepared by subsequent reduction of the keto-group. Moreover, any benzyl group present may be subjected to a subsequent substitution reaction to produce a further R' or R'' group.

Pharmaceuticals having an anti-arrhythmic effect are known in the art. However, these known compounds have adverse side effects, such as a negative effect on the contractility of the heart. Accordingly, the use of these preparations is not without problems and requires a careful evaluation of the risks involved [cf. for example, Muertz et al., Med.Mschr. 24, 239–245 (1970) and Bleifeld et al., Dtsch. Med. Wschr. 96, 671–680 (1971)].

Thus, known anti-arrhythmic preparations such as Antazolin, Lidocain and N-propylajmalin must be used with great care in view of their narrow therapeutic range, that is to say there is only a relatively small difference between the doses which produce an anti-arrhythmic effect and the doses which produce a negative inotropic effect.

It has now been found that the new bispidine and bispidone derivatives are suitable for the treatment of defects in the function of the heart and have a greater therapeutic range than these known compounds.

The anti-arrhythmic effect of the new compounds was shown by determining the functional refractory period of the left auricle of the heart of guinea pigs. The experimental procedure utilized paired electrical stimulation in an adaptation of the method of W. C. Govier, J. Pharmacol. Exp. Therap. 148, 100–105 (1965). In this model, the numerous known anti-arrhythmical preparations of differing structure and point of therapeutic attack all show an prolongation of the functional refractory period. The experiment additionally permits a study of the effects of different substances on the contractility of the heart muscles [Reuter und Heeg, Naunyn, Naunyn-Schmiedeberg's Arch. Pharmakol. 268, 323–333 (1971); Zetler and Strubelt, Naunyn-Schmiedeberg's Arch. Pharmakol. 271, 335–345 (1971).] Therefore the experiment is suitable for discovering which substances have the greatest therapeutic range, that is to say, which have the greatest safety margin between the anti-arrhythmic and the negatively inotropically effective dosages.

To test the substances, up to 18 and 30 individual experiments were carried out in each case. At least 3 dosages were tested each on 6 auricle preparations and the linear regression functions were calculated [A. Lindner: Statistische Methoden, 3d Edition, Birkhaeuser Verlag, Basel (1969)], whereby the maximum percentage deviations from the initial value in the period of up to 30 minutes from the addition of the test substance to the bath liquid were used.

In Table 1, the effects of two typical representatives of the compounds according to the present invention are compared with those of known anti-arrhythmically effective compounds. In column II, the anti-arrhythmic effect is shown and in column III, the inotropic effect is shown. In column IV, the therapeutic range of the compounds is shown. The ED$_{25}$ is the effective dose which extends the refractory period by 25% or lowers the contractional force by 25%, respectively. The Table shows that the substances in accordance with the present invention are clearly superior to the known substances both with regard to safety margin between the desired rhythm regulating effect and the undesired impairing of the contractional forces of the heart.

TABLE 1

| I<br>Anti-arrhythmically effective substances | II<br>Anti-arrhythmic effect<br>(Refractory period extension) | III<br>Inotropic effect<br>(Contraction force lowering) | IV<br>Therapeutic Breadth<br>(III/II) |
|---|---|---|---|
| N-isopropyl-N'-β-phenylethyl-bispidine | ED$_{25}$ = 0.13 | ED$_{25}$ = 0.26 | 2.0 |
| N,N'-dibenzyl-bispidine | ED$_{25}$ = 0.034 | ED$_{25}$ = 0.07 | 2.0 |
| Lidocain | ED$_{25}$ = 0.47 | ED$_{25}$ = 0.48 | 1.0 |
| N-n-propylajmalin | ED$_{25}$ = 0.0037 | ED$_{25}$ = 0.0015 | 0.4 |
| Antazolin | ED$_{25}$ = 0.164 | ED$_{25}$ = 0.094 | 0.6 |

The anti-arrhythmic potency of bispidine derivatives could also be shown by their effect on experimentally induced heart rhythm disturbances in intact experimental animals. If rats are continuously infused intravenously with aconitine, then serious disturbances of the cardiac rhythm such as extrasystole, ventricular tachycardia, and ventricular flutter, which finally lead to the death of the experimental animals, can be observed on an electrocardiogram. By pre-treatment with, for example, N-isopropyl N'-β-phenylethyl-bispidine or N,N'-dibenzyl bispidine, the occurrence of these heart rhythm disturbances is prevented or at least substantially delayed even if aconitine is continuously injected. This experimental arrhythmic model is checked by means of clinically tested standard therapeutic compounds as to its reliability and is well suited for characterizing antiarrhythmical compounds in experiments on animals [cf. for example, Bianci et al., Arzneim.-Forsch. 18, 845–850 (1968); Haas und Busch, Arzneim.-Forsch. 18, 401–407 (1968); Haas et al., Arzneim.-Forsch. 21, 1392–1399 (1971); Marmo, Naunyn-Schmiedeberg's Arch. Pharmakol. 269, 231–247 (1971); and Strubelt et al., Naunyn-Schmiedeberg's Arch. Pharmakol. 271, 346– 360 (1971.]

Table 2 shows the result of this test. The $ED_{25}$ or $ED_{50}$ are the intravenous dosages in mg/kg which allow an increase in administered aconitine doses, relative to the control, by 25 or 50%, respectively, before the occurrence of extrasystoles, ventricular tachycardia, and ventricular flutter.

TABLE 2

| | | N,N'-dibenzyl bispidine | N-isopropyl N'-phenyl-ethyl-bispidine | Spartein |
|---|---|---|---|---|
| Extrasystoles | $ED_{25}$ | 1.06 | ca 1.8 | +) |
| | $ED_{50}$ | 1.76 | ca 2.3 | +) |
| Ventricular Tachycardia | $ED_{25}$ | 0.87 | 1.41 | 4.43 |
| | $ED_{50}$ | 1.23 | 2.13 | 9.55 |
| Ventricular flutter | $ED_{25}$ | 1.03 | 1.7 | +) |
| | $ED_{50}$ | 1.48 | 2.47 | +) |

+) no significant effect obtainable

This Table also shows the superior effect of the substances in accordance with the present invention when administered intravenously. Moreover, the antiarrhythmic compounds according to the present invention are about 10 times more effective than procainamide when administered orally. Furthermore, in contrast to known anti-arrhythmic compositions, they have no blood pressure lowering effect.

The new compounds may be administered orally, intravenously, and intramuscularly. The effective dose lies within the range of 1 to 10 mg/kg per day when given orally and within the range of 0.05 to 1.0 mg/kg per day when administered intravenously or intramuscularly. The compounds may be administered in any suitable form, such as, for example, tablets, coated tablets, lozenges, and solutions.

The synthesis of the claimed bispidones by a Mannich reaction is suitably performed, in a manner known in the art, in an inert organic solvent in the presence of an organic or inorganic acid. Tetrahydrofuran, chloroform, methylene chloride and, particularly, methanol, ethanol, and isopropanol are suitable solvents for the reaction medium. Glacial acetic acid and hydrochloric acid are the acids which are preferably utilized in the reaction. The formaldehyde may, if desired, be in the form of paraformaldehyde. It is advantageous if the reaction is effected at an elevated temperature, such as the boiling point of the solvent or solvents being employed.

If the product thus obtained is one in which R' or R'' represents a benzyl group, then the benzyl group may be removed by known techniques for catalytic hydrogenation. The amine thus obtained may be alkylated or aralkylated, as known in the art, with a halogen compound of the formula R' -Hal or R'' -Hal, wherein R' and R'' are as aforementioned and Hal represents a halogen atom, preferably a chlorine atom. The reaction with the halo-compound is preferably carried out in the presence of an alkali metal carbonate in an inert solvent having a relatively high boiling point, such as xylene or methyl isobutyl ketone.

Bispidines are prepared by reduction of the corresponding bispidones by techniques known in the art, for example using hydrazine hydrate in basic solution.

The bispidones and bispidines can be salified with a physiologically compatible acid, as known in the art. Physiologically compatible salts include those obtained from hydrochloric acid, sulfuric acid, phosphoric acid, fumaric acid, maleic acid, succinic acid, tartaric acid, or citric acid, among other suitable acids known in the art.

A better understanding of the present invention and of its many advantages will be had by referring to the following specific examples, given by way of illustration.

EXAMPLE 1

N,N'-dibenzyl bispidone

Paraformaldehyde (63 g) was suspended in a mixture of methanol (1000 ml), benzylamine (107 g), and glacial acetic acid (62 g) in a three-necked flask having a capacity of four liters. This mixture was boiled under reflux and, over a period of 30 minutes, a solution of N-benzylpiperidone-4 (189 g) and glacial acetic acid (60 g) in methanol (700 ml) was added dropwise, with stirring. After a further three hours, the solvent was completely removed by distillation. The residue was rendered highly alkaline with a solution of potassium hydroxide (126 g) in water (140 ml) and the organic components were then extracted with methylene chloride. After removal of the solvent by evaporation, distillation of the residue was effected in vacuo. The distillate thus obtained (292 g) was re-distilled. At 1850 C/0.15 mm Hg, 190 g (approximately 60% of the theoretical yield) of analytically pure N,N'-dibenzylbispidone were obtained. This solidified on standing and, when recrystallized from petroleum ether of low boiling point, melted at 70° to 71°C.

EXAMPLE 2

N,N'-dibenzylbispidine

In a three-necked flask of 1 liter capacity, N,N'-dibenzylbispidone (95 g) and potassium hydroxide (98 g) were mixed with triethyleneglycol (650 ml). While stirring slowly, hydrazine hydrate (65 g; 80 %) was added dropwise. The mixture was heated slowly and then boiled under reflux for 3 hours. Subsequently, the volatile components were distilled off, until the internal temperature had risen to 220°C. After cooling, both the distillate and the residue were diluted with 600 ml water, and were thoroughly extracted with ether. After drying with sodium sulfate and evaporation of the ether, vacuum distillation was effected. At 178° to 183°C/0.35 mm Hg, analytically pure N,N'-dibenzylbispidine (68.5 g, 75.5% of the theoretical yield) distills over.

The hydrochloride melts at 84° to 86°C, when recrystallized from isopropanol.

In a manner analogous to that described in Example 1, there were produced substituted bispidone derivatives of the general formula:

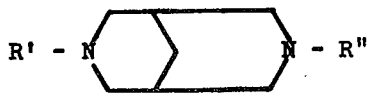

EXAMPLE 4

N-(4,4-diphenylbutyl) N'-methyl bispidine

N-methylbispidine (14 g, 0.1 mol) was boiled under reflux with stirring for 5 hours with 4,4-diphenyl butyl chloride (24.5 g, 0.1 mol) and potassium carbonate (13.8 g, 0.1 mol) in xylene (250 ml). The reaction product was cooled and mixed with water. The organic phase was separated and dried with anhydrous sodium sulfate, the solvent distilled off, and the residue distilled in vacuo.

A yield of 22.9 g, representing 66% of the theoretical yield, of N-(4,4-diphenylbutyl) N'-methylbispidine having a boiling point of 190°C/0.2 mm Hg was obtained.

EXAMPLE 5

Tablets of the following composition were produced in a known manner in a tablet press:

TABLE 3

| R' | R'' | Yield (% of theoretical yield) | Boiling point (°C/mm Hg) | Melting Point (°C) |
|---|---|---|---|---|
| CH₃ | n-hexyl | 58.9 | 92–95/0.1 | |
| CH₃ | benzyl | 32.1 | 127–135/0.1 | 63 |
| CH₃ | β-phenylethyl | 15.2 | 148–151/0.1 | 72 |
| Isopropyl | β-phenylethyl | 47.5 | | 81–83 |
| Phenylethyl | phenylethyl | 24.4 | 185–210/0.08 | |

In a manner analogous to that described in Example 2, there were produced substituted bispidine derivatives of the general formula:

TABLE 4

| R' | R'' | Yield (% of theoretical yield) | Boiling Point (°C/mm Hg) |
|---|---|---|---|
| CH₃ | n-hexyl | 59.5 | 148/15 |
| CH₃ | benzyl | 73.2 | 107–108/0.5 |
| Isopropyl | β-phenylethyl | 23.3 | 121/0.12 |
| Phenylethyl | phenylethyl | 32.7 | 157–165/0.01 |

EXAMPLE 3

N-diphenylmethyl-N'-methyl bispidine

N-methylbispidine (14 g, 0.1 mol), produced by debenzylation from N-benzyl N'-methylbispidine using a Pd-C-catalyst was boiled under reflux, with agitation, with 24.7 g (0.1 mol) benzhydryl bromide (24.7 g, 0.1 mol) and potassium carbonate (13.8 g, 0.1 mol) in methyl isobutyl-ketone (250 ml) for 24 hours. The reaction product was cooled and mixed with water, the organic phase being separated and evaporated. The residue was distilled in a high vacuum. The oil solidified on standing and was recrystallized from di-isopropylether. A yield of 24.8 g (81 % of the theoretical yield) of N-diphenylmethyl N'-methyl bispidine having a melting point of 66°C and a boiling point of 150° to 155°C/0.01 mm Hg was obtained.

| | |
|---|---|
| N,N'-dibenzyl bispidine | 50.00 mg |
| Corn starch | 120.00 mg |
| Talc | 25.20 mg |
| Silica gel ("Aerosil") | 1.50 mg |
| Cetyl alcohol | 3.00 mg |
| Myristyl alcohol | 0.30 mg |
| | 200.00 mg |

EXAMPLE 6

N-isopropyl N'-β-phenylethyl bispidine (10 g) was dissolved in water (5000 ml), with the addition of NaCl and an equimolecular quantity of acetic acid, so as to form a blood isotonic solution. The solution was filled into 5 ml ampules and sterilized.

What is claimed is:

1. A compound of the formula wherein R is =C=O or —CH₂—, R' is lower alkyl optionally substituted by phenyl, and R'' is lower alkyl optionally substituted by one or two phenyl groups, with the proviso that R' and R'' together contain at least six carbon atoms, and physiologically compatible salts thereof.

2. A compound as in claim 1 which is N,N'-dibenzyl bispidone.

3. A compound as in claim 1 which is N-methyl N'-n-hexyl bispidone.

4. A compound as in claim 1 which is N-methyl N'-benzyl bispidone.

5. A compound as in claim 1 which is N-methyl N'-β-phenylethyl bispidone.

6. A compound as in claim 1 which is N-isopropyl N'-β-phenylethyl bispidone.

7. A compound as in claim 1 which is N,N'-diphenylethyl bispidone.

8. A compound as in claim 1 which is N,N'-dibenzyl bispidine.

9. A compound as in claim 1 which is N-methyl N'-n-hexyl bispidine.

10. A compound as in claim 1 which is N-methyl N'-benzyl bispidine.

11. A compound as in claim 1 which is N-isopropyl N'-β-phenylethyl bispidine.

12. A compound as in claim 1 which is N,N'-diphenylethyl bispidine.

13. A compound as in claim 1 which is N-diphenylmethyl N'-methyl bispidine.

14. A compound as in claim 1 which is N-(4,4-diphenylbutyl) N'-methyl bispidine.

15. An anti-arrhythmic composition comprising a pharmacologically effective amount of at least one compound as claimed in claim 1 in association with a therapeutically acceptable carrier.

* * * * *